(12) United States Patent
Schubert et al.

(10) Patent No.: US 8,884,243 B2
(45) Date of Patent: Nov. 11, 2014

(54) RADIATION PHANTOM

(75) Inventors: Elko Schubert, Gross-Umstadt (DE);
Peter Steidl, Dornburg (DE); Daniel Richter, Darmstadt (DE); Christoph Schuy, Langen (DE); Christoph Bert, Uttenreuth (DE)

(73) Assignee: GSI Helmholtzzentrum fuer Schwerionenforschung GmbH, Darmstadt (DE)

( * ) Notice: Subject to any disclaimer, the term of this patent is extended or adjusted under 35 U.S.C. 154(b) by 0 days.

(21) Appl. No.: 13/991,656

(22) PCT Filed: Nov. 17, 2011

(86) PCT No.: PCT/EP2011/070337
§ 371 (c)(1),
(2), (4) Date: Jul. 23, 2013

(87) PCT Pub. No.: WO2012/076311
PCT Pub. Date: Jun. 14, 2012

(65) Prior Publication Data
US 2013/0292580 A1 Nov. 7, 2013

(30) Foreign Application Priority Data
Dec. 8, 2010 (DE) .......................... 10 2010 061 121

(51) Int. Cl.
*G01J 1/42* (2006.01)
*A61N 5/10* (2006.01)

(52) U.S. Cl.
CPC ....... *A61N 5/1048* (2013.01); *A61N 2005/1076* (2013.01); *A61N 5/1037* (2013.01); *A61N 2005/1072* (2013.01); *A61N 2005/1087* (2013.01)
USPC .......................................................... 250/395

(58) Field of Classification Search
CPC ............................................. A61N 2005/1076
USPC .......................................................... 250/395
See application file for complete search history.

(56) References Cited

U.S. PATENT DOCUMENTS

| | | | |
|---|---|---|---|
| 6,697,451 B2 * | 2/2004 | Acharya et al. | 378/18 |
| 2005/0151071 A1 * | 7/2005 | Nilsson | 250/252.1 |
| 2005/0211889 A1 | 9/2005 | Varchena et al. | |
| 2008/0011946 A1 | 1/2008 | Suh et al. | |
| 2008/0298540 A1 | 12/2008 | Serban et al. | |
| 2009/0110140 A1 | 4/2009 | Krautim et al. | |

OTHER PUBLICATIONS

Brusasco C et al: 11A dosimetry system for fast measurement of 3D depth-dose profiles in charged-particle tumor therapy with scanning techniques 11 Nuclear Instruments & Methods in Physics Research, Section—B:Beam Interactions With Materials and Atoms, Elsevier, Amsterdam, N L, vol. 168, No. 4, Aug. 1, 2000, pp. 578-592.

(Continued)

*Primary Examiner* — Kiho Kim
(74) *Attorney, Agent, or Firm* — Leydig, Voit & Mayer, Ltd.

(57) ABSTRACT

A radiation phantom device includes at least one movement device for moving at least one first sub-region of the radiation phantom device. The radiation phantom device has, at least one of at times or in regions, radiation properties which are in conformity with a radiation phantom model.

18 Claims, 3 Drawing Sheets

(56) References Cited

OTHER PUBLICATIONS

Krager et al: "A System for the Three-Dimensional Dosimetric Verification of Treatment Plans in Intensity-Modulated Radiotherapy With Heavy Ions" Oct. 1999, pp. 2125-2132.

Knopf et al: "Special Report: Workshop on $D-Tratment Planing in Actively Scanned Particle Therapy—Recommendation, Technical Challenges and Future Research Directions" Sep. 2010, pp. 4608-4614.

* cited by examiner

RADIATION PHANTOM

CROSS REFERENCE TO RELATED APPLICATIONS

This application is a U.S. National Phase application under 35 U.S.C. §371 of International Application No. PCT/EP2011/070337, filed on Nov. 17, 2011, and claims benefit to German Patent Application No. DE 10 2010 061 121.2, filed on Dec. 8, 2010. The International Application was published in German on Jun. 14, 2012, as WO 2012/076311 A1 under PCT Article 21 (2).

FIELD

The invention relates to a radiation phantom device, in particular to a radiation phantom device for validating a radiation process, preferably for validating radiation planning, which comprises at least one movement device for moving at least one first sub-region of the radiation phantom device, in particular relative to at least one second sub-region of the radiation phantom device. The invention further relates to a method for validating a radiation process, in particular for validating radiation planning, the radiation process taking place on a radiation phantom device which comprises at least one movement device for moving at least one first sub-region of the radiation phantom device, in particular relative to at least one second sub-region of the radiation phantom device.

BACKGROUND

Irradiating articles with ionising radiation makes it possible to load them with a particular radiation dose, including internally. In this context, depending on the radiation used and the purpose, there is more or less spatially unresolved radiation (that is to say, the body is loaded with a substantially equal radiation dose substantially over the whole volume region thereof), surface-resolved radiation (that is to say, there is structured loading as a function of the x and y coordinates in a plane, but no structured radiation in terms of depth or in the z direction) or else even three-dimensionally structured radiation (that is to say, radiation with spatial resolution in all three spatial directions).

Radiations in the medical field are one example application among many radiations of this type. In the meantime, the spectrum for a use of ionising radiation in medicine varies over a wide range. For example, X-rays in which a patient is loaded with substantially unstructured radiation have been established as a diagnosis method for many years. Depending on the type of tissue which is irradiated (for example soft tissue, bone, air cavities and the like), the X-ray radiation is weakened by varying amounts, and the X-ray film located behind the patient is thus blackened by different amounts. An example application of three-dimensionally structured radiation is the treatment of tumours with particle radiation. Photons and electrons are sometimes used for this purpose. In recent years, however, the treatment of tumours using heavy ion radiation has also been developed considerably, since heavy ion radiation, because of the distinctive Bragg peak thereof, provides an excellent opportunity to implement precise structuring in terms of depth (in the z-direction; parallel to the particle beam), in the millimeter range.

In particular in cancer treatment, it is necessary to introduce a particular, comparatively high, cell-damaging dose into a volume region located inside the body (namely at the location of the tumour to be treated), whereas the remaining tissue of the patient should experience as weak a radiation dose as possible. This is the case in particular for critical tissue regions (often designated as OAR, "organ at risk"), in which particular (generally relatively low) maximum radiation doses must not be exceeded under any circumstances. Critical tissue regions of this type are for example nerve tissue, blood vessels, particular internal organs and the like.

So as to be able to introduce three-dimensionally structured radiation of this type, the radiation process has to be adjusted suitably (for example in terms of beam guidance, particle energy and the like). Since in the meantime what are known as scanning methods have become established, in which a pencil-thin particle beam (known as a "pencil beam") departs from rows, columns and layers of the tissue to be treated in succession, a set of parameters which are to be applied in temporal succession may also be required for controlling the radiation device (in a manner varying over time). In practice, comprehensive calculations are required for this purpose, particular assumptions and empirical values (which are not necessarily exactly correct) also contributing to the calculations. So as to be certain that the obtained parameters are correct, what are known as radiation phantoms have already been in use for some time. For checking purposes, they are loaded with the radiation, instead of the patient. Only when the radiation result is satisfactory is the obtained radiation plan actually introduced to the patient.

Particular requirements—both in terms of the radiation phantom and in terms of the requirements on the calculation of a radiation plan—come up when movements also have to be taken into account. This is the case for example if the tumour moves perceptibly during the treatment. This is the case for example if the tumour is located in or adjacent to the lung, in or adjacent to the heart or on or adjacent to the intestine.

In the meantime, a wide range of methods have been proposed so as to be able to obtain a radiation plan even with constraints of this type. A summary is found for example in the publication "Special report: workshop on 4D-treatment planning in actively scanned particle therapy—recommendation, technical challenges, and future research directions", by A. Knopf, C. Bert, E. Heath, S. Nill, K. Kraus, D. Richter, E. Hug, E. Pedroni, S. Safai, F. Albertini, S. Zenklusen, D. Boye, M. Söhn, N. Soukup, B. Sobotta and A. Lomax in Med. Phys. 37 (9), September 2010, pages 4,608-4,614.

Although the above-disclosed calculation methods and radiation devices are very promising, the problem still remains of checking the quality thereof in advance, before an animal or a human is loaded with the planned dose in accordance with the radiation plan.

There are thus a wide range of radiation phantoms to date, but they are often not movable, in particular not internally movable. In cases where movements can be simulated, the metal components which are conventionally used in this case are found to be problematic, since they make either the actual radiation process or else at least the measurement processes difficult, or even impossible, and the data thus obtained can be worsened to the point of becoming unusable. Moreover, the movements which can be represented in radiation phantoms known thus far are often found to be insufficient. For example, in many known radiation phantoms merely 1D movement can be represented.

SUMMARY

In an embodiment, the present invention provides a radiation phantom device includes at least one movement device for moving at least one first sub-region of the radiation phantom device. The radiation phantom device has, at least one of at times or in regions, radiation properties which are in conformity with a radiation phantom model.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
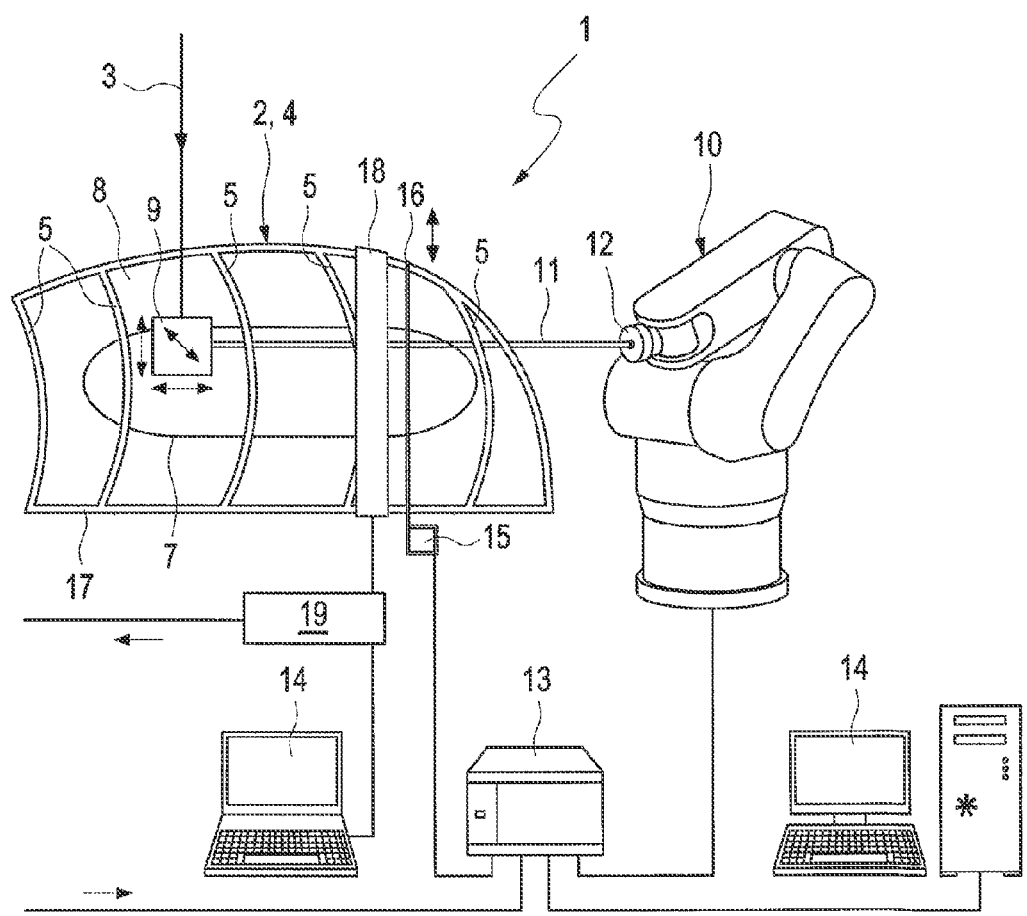
FIG. 1 is a schematic overview of an embodiment of a radiation phantom measurement construction.

An aspect of the invention is to provide a radiation phantom device which is improved by comparison with known radiation phantom devices. A further aspect of the invention is to provide a method for validating a radiation process which is improved by comparison with known methods for validating radiation processes.

In an embodiment, the present invention provides a radiation phantom device, which comprises at least one movement device for moving at least one first sub-region of the radiation phantom device, in such a way that the radiation phantom device has radiation properties in conformity with the radiation phantom model at least at times and/or at least in regions. The radiation phantom device may in particular be a radiation phantom device for validating a radiation process. Preferably, the radiation phantom device may be a radiation phantom device for validating a radiation plan. The movement of at least one first sub-region of the radiation phantom device may preferably take place relative to at least one second sub-region of the radiation phantom device. The radiation phantom device may in principle be any type of radiation phantom. Thus, in this connection, biological samples such as cell cultures or the like are conceivable. In this context, it is perfectly possible for the cell cultures to be used in a spatially resolved manner, for example in that a two-dimensional or three-dimensional arrangement (array) of individual, mutually separated cell culture samples is used. By analysing how strongly which sample part or which sub-samples are damaged, a spatially resolved measurement can accordingly be taken. However, other detector types are conceivable, and generally preferred, such as film detectors (the degree of blackening of the corresponding films typically being used as the measurement value for the radiation input), semiconductor detectors, ionisation detectors and the like. Naturally, these and further detector types can be used with two-dimensional or three-dimensional spatial resolution. A combination of these "other" detector types and "biological" detector types may also be found to be advantageous. Preferably, in addition to the aforementioned detector units, the radiation phantom device also comprises "passive" regions, which may for example simulate the presence of tissue, other material segments and the like. The at least one movement device may also be constructed in any desired manner. The manner of operation (for example electrical, pneumatic, hydraulic and the like) can also in principle be selected as desired. It is possible that the movement means may be controlled for example by way of external control signals. This is preferably possible within a wide range. In particular, it is conceivable for the movement to be switched on and off. However, it is also conceivable for the speed of a movement to be adjustable. It is further advantageous if substantially any desired movements can be carried out at substantially any desired speeds (it being possible for the upper limit of the speeds to be defined in particular by way of the radiation phantom model, optionally with the addition of a safety margin). Preferably, the movement device is configured in such a way that it makes non-standard movement cycles possible as well as a standard movement cycle and/or can modify the standard movement cycle. Purely by way of example, this may represent the patient's breathing. The movement cycle is typically relatively constant for an individual patient. Nevertheless, it is possible that the patient may breathe more rapidly and/or deeply during the actual radiation because of nervousness (or of course also more slowly and/or shallowly). Accordingly, adaptation of the standard movement cycle is expedient. Further, it may be found to be advantageous if movements having different parameters are superposed on one another to some extent. This may take place both by controlling an individual movement device accordingly and by using a plurality of movement devices. In this context, parameters of this type are in particular the respective movement phase, period and/or amplitude. A tumour located on the lung may be mentioned here purely by way of example. The ribcage (thorax) moves for example at a particular amplitude A1 and phase B1. The actual tumour, by contrast, has a movement with a different amplitude A2 and phase B2. The two movements having the respective amplitudes A1 and A2 and the respective phases B1 and B2 are thus superposed on one another, and produce a relatively complex overall movement pattern. Furthermore, it is also possible that the patient may make irregular movements, such as those induced by coughing, hiccoughing or the like, during the radiation. Accordingly, it is advantageous if the radiation phantom device can also simulate irregular movements of this type. All of the aforementioned movements (in particular cyclically recurring movements) can for example be produced at least in part using "hardware assemblies" (for example cam transmissions and the like). However, it is preferred if the movement device can be controlled in substantially any desired manner, for example by using suitable adjustment pulses. In this case, the radiation phantom device is capable of particularly universal use. In this context, the movement which is carried out by at least one movement device may not only be a movement with respect to the external spatial coordinates. It is particularly advantageous (because this is typical of many radiation processes) if the movement of the moved first sub-region takes place relative to at least one second sub-region of the radiation phantom device. This may for example be the movement of a tumour located in the lung tissue relative to most of the body regions (such as the spinal column and the like). In this context, the (relative) movement may relate to one, two or preferably three spatial directions (translational degrees of freedom). In addition or alternatively, one, two or three rotational movements (rotational degrees of freedom) may be involved. Furthermore, in particular, contraction and/or expansion of tissue may also expediently be simulated. However, enlargement or reduction of cavities, which are located in particular between at least one first sub-region and at least one second sub-region, may also be found to be advantageous in the radiation phantom device, since this too may occur in reality (for example in the case of lung tumours). Naturally, any desired mixed forms of the aforementioned (and other) forms of movement are also conceivable. The term "in conformity with the radiation phantom model" should be understood in particular to mean that the radiation phantom "conforms" to the "model" thereof. In this context, the model is generally the device—the article or else the animal or person—which is to be "simulated" by the radiation phantom device. In this context, the "conformity" relates in particular to the relevant properties, and generally means that the effects brought about by these properties are at least similar, preferably substantially identical. In the present context, a property of this type should be understood to mean in particular the influence on applied radiation (a "radiation property"). A "radiation property in conformity with the radiation phantom model" should be understood to mean in particular a property of the radiation phantom device, with respect to the applied radiation, such that it approximates the model which is to be simulated by the radiation phantom device as closely as possible in terms of the effects thereof on the applied radiation. This may relate in particular to a particularly good qualitative and/or quantitative approximation. If there is a (broad or sufficient) conformity with the radiation phantom model, it is possible in particular that the radiation phantom device has properties which make absolute dosimetry possible using an ion beam and/or using another type of radiation. The radiation may in particular be ionising radiation, such as gamma radiation, X-ray radiation and particle radiation (leptons and hadrons, in particular electrons, positrons, protons, helium ions, carbon ions, oxygen ions, nitrogen ions, neon ions). In this context, in particular in the case of "therapeutic radiation" (that is to say for example ion radiation or heavy ion radiation), the model conformity of the radiation phantom device preferably relates to the conformity in the region of a detector means (which need not necessarily be positioned inside the radiation phantom device) and/or of a region positioned proximally in front of the detector means. In particular in the case of "measurement radiation" (for example X-ray radiation, CT radiation and the like), the model conformity of the radiation phantom device preferably relates to the conformity in the region of a detector means and/or to the conformity in a region in the form of an axially positioned disc and/or (especially in the case of a cone beam geometry) to the conformity in a cone-shaped (frustum-shaped) region. This is because (critical) regions of this type are generally the target of the analyses. Distortions in regions at a distance therefrom typically have no effect, no measureable, significant and/or relevant effect, and/or a comparatively small effect on the radiation measurement in the region of the detector means and/or the target volume region. Accordingly, by way of a potentially simple and/or more cost-effective construction of the radiation phantom device in the remote regions, costs can be reduced or the technical functionality of the radiation phantom device can be increased.

Preferably, the radiation phantom device is constructed in such a way that it has radiation properties which are in conformity with the radiation phantom model at least at times and/or at least in regions and/or measurement radiation properties which are in conformity with the radiation phantom model at least at times and/or at least in regions. The radiation beam properties which are in conformity with the radiation phantom model relate in particular to the properties of the radiation phantom device with respect to the actual treatment beam. This is generally a particle beam, such as in particular an electron beam, a positron beam, a proton beam, a helium ion beam, a carbon ion beam, an oxygen ion beam, a nitrogen ion beam, another ion beam and/or another heavy ion beam. However, photons are sometimes also used, such as in particular in what is known as IMRT (intensity-modulated radiation therapy), which has in the meantime become established as what is known as an IMPT (intensity-modulated particle therapy), including in the case of heavy ion or proton treatment. The measurement beam properties in conformity with the radiation phantom model are in particular the properties of the radiation phantom device with respect to measurement radiation, which is used in particular for checking purposes (such as for checking the position of the tumour region and/or other material regions or tissue regions). This may in particular involve conventional X-ray beams (for example open fields at <250 keV). Optionally, however, this may also involve nuclear spin tomography and/or computer tomography methods (in particular kV, MV and/or cone beam computer tomography methods) and/or other radiation used especially for imaging. Naturally, other methods are also conceivable which are based on measurement radiation, in particular on penetrating measurement radiation, particularly preferably on ionising measurement radiation. Conventionally, the use of measurement radiation of this type is found to be advantageous because, for example, by way of the data thereby obtained the ion dose to be expected can be calculated and/or precise mounting of the radiation phantom device (analogously to the subsequent patient) becomes possible at the radiation site.

It is advantageous in particular if there are weakening properties which are in conformity with the radiation phantom model and/or secondary radiation emission properties which are in conformity with the radiation phantom model and/or scattering properties which are in conformity with the radiation phantom model at least at times and/or at least in regions. In particular, this may relate to sub-regions of the radiation phantom device which are positioned adjacently and/or proximally (especially in relation to "treatment radiation", that is to say usually the "actual" radiation beam) and/or axially in a disc shape (especially in relation to CT measurement radiation) and/or in a cone shape (especially in relation to cone beams) and/or in a fan shape (especially in relation to fan beams) with respect to a target volume region. In this context, the target volume region is generally the position of the "tumour", where at least one detector device is generally arranged in the radiation phantom device. If the aforementioned properties (weakening properties, secondary radiation emission properties and/or scattering properties) of the radiation phantom device come particularly close to the radiation phantom model (to the "original"), the quality of the radiation process validation can generally turn out particularly high. If there are deviating properties, the weakening of the radiation used (in particular treatment radiation and/or measurement radiation) should be considered in particular. As regards the secondary radiation emission properties, the more frequently occurring effect should be considered whereby the radiation used (in particular measurement radiation and/or treatment radiation) can release particles during interactions with particular materials, the "input radiation" generally being weakened in the process. The released particles may in particular be neutrons, electrons, positrons, protons and the like. As regards scattering properties, not only the angular deflection and/or angular extension of the radiation used (in particular treatment radiation and/or measurement radiation) should be considered, but also scattering mechanisms in which additional effects occur, such as the release of particles (for example Compton electrons).

It may further be found to be advantageous if the radiation phantom device has reflection properties which are in conformity with the radiation phantom model and/or secondary radiation emission properties which are in conformity with the radiation phantom model and/or scattering properties which are in conformity with the radiation phantom model at least at times and/or at least in regions. This applies in particular to sub-regions of the radiation phantom device which are positioned adjacently and/or distally (especially in relation to "treatment radiation") and/or axially in a disc shape (especially in relation to CT measurement radiation) and or in a cone shape (especially in relation to cone beams) and/or in a fan shape (especially in relation to fan beams) with respect to a target volume region. The aforementioned influences typically have a particularly large effect on the target volume region or regions if they are positioned adjacently and/or distally with respect to the corresponding target volume region. By way of a corresponding approximation of the radiation phantom device to the radiation phantom model (that is say to the "original"), a generally particularly high quality of the validation of the radiation process can again be achieved. Moreover, as regards reflector properties, mechanisms should particularly be considered in which an effect occurs in the "reverse direction" at least in part. This may for example involve scattering mechanisms and the like in which at least part of the starting radiation is radiated backwards in a particular direction (that is to say in particular scattered by usually more than 90°, more than 120° and/or more than 150°).

Preferably, the radiation phantom device is formed in such a way that at least one movement device can carry out a multi-dimensional movement at least at times and/or at least in regions, in particular at least a 2D movement, at least a 3D movement, at least a 4D movement, at least a 5D movement and/or at least a 6D movement. In this way, the radiation phantom device is capable of particularly universal use. As stated previously, the dimensions may in particular be translational movements and/or rotational movements. However, it is also conceivable for the radiation phantom device not to be moved at least at times and/or at least in regions and/or merely to carry out a one-dimensional movement. As regards all of the aforementioned movements and/or non-movements, time-dependency of the movement should naturally be considered. Depending on the use of language, it would accordingly also be possible to refer to a movement having a dimension increased by one, ultimately potentially resulting in up to "seven-dimensional movements". Furthermore it is possible—and generally preferred—for one or more movement devices to produce mutually superposed individual movements (that is to say for example a superposition of a breathing movement on a heartbeat movement and/or another movement).

It is particularly advantageous for the radiation phantom device to comprise at least one movement transmission means, which has radiation properties which are in conformity with the radiation phantom model at least at times and/or at least in regions. The inventors have found that it is very difficult or virtually impossible to produce the movement directly in the radiation phantom, and in particular adjacent to the target volume region. This is in particular due to the fact that movement production means known in the prior art generally comprise metal at least in part. However, metal is generally not in conformity with the radiation phantom model in terms of the radiation properties thereof. More generally speaking, (relatively high concentrations of) materials having high atomic numbers are to be avoided. In particular, the atomic number should be lower than the atomic numbers of light metals (such as for example aluminium, copper and/or iron). However, to their own surprise, the inventors have found that it is not problematic for a movement which is produced sufficiently far away to be transmitted, using movement transmission means, to a location at which the movement (or the force) should advantageously be applied. On the contrary, movement transmission means of this type are relatively simple to form in such a way that they have radiation properties in conformity with the radiation phantom model. Some components of this type are even commercially available.

In particular, it is advantageous if at least one rod means and/or at least one chain means and/or at least one belt means and/or at least one rope means and/or at least one screw drive means and/or at least one gearwheel drive means is provided in the radiation phantom device and/or at least one plastics material in conformity with the radiation phantom model is used in the radiation phantom device. Force transmission means of this type or plastics materials of this type have been found in initial tests to be particularly advantageous. In particular, by means thereof the required movements can be transmitted particularly advantageously or properties particularly in conformity with the radiation phantom model can be implemented using suitable plastics materials. In particular, it is possible to form the aforementioned force transmission means at least in part from plastics materials which are in conformity with the radiation phantom model.

It is further advantageous for at least one movement production means to be provided in the radiation phantom device. The movement production means may in particular be at least one electric motor means, at least one stepper motor, at least one linear motor, at least one hydraulic means, at least one pneumatic means and/or at least one robot arm means. Using a movement production device, the movements required for moving the radiation phantom device can advantageously be produced "on site" or in the direct vicinity thereof. The aforementioned movement production devices in particular have been found in initial tests to be particularly advantageous. Very generally, it has been found to be advantageous for the movement production devices to be able to be moved in substantially any directions and/or at substantially any speeds (in particular those which can realistically be achieved by the model; optionally plus a safety margin) when controlled using a corresponding control signal. In this way, particularly flexible use of the radiation phantom device is possible. In particular, in this case "mutually superposed" movements can also be produced using merely one or a reduced number of movement devices. The robot arm means may be a conventional commercial industry robot (or a part thereof). It is also preferable for at least one movement production device to comprise a measurement sensor (for example an absolute encoder or a relative measurement sensor). Naturally, it is possible also to provide a plurality of movement devices, for example so as to produce "mutually superposed" movements.

It is further advantageous for at least one movement means in the radiation phantom device to be formed as a rapid movement means and/or as an aperiodic movement device. With movement devices of this type, in particular even irregular movement patterns such as coughing and the like can be simulated. Accordingly, the resulting radiation phantom device is capable of particularly universal use, and this is advantageous.

It is further advantageous for the radiation phantom device to imitate a real, in particular real biological model at least at times and/or at least in regions, and particularly preferably to comprise at least implant means at least at times and/or at least in regions. In this way, the radiation phantom device is capable of particularly universal use and particularly predictive radiation process validations can be carried out. Purely by way of example, this could thus involve a type of chest model comprising rib replacement material, tissue replacement material and the like, if the radiation of a tumour in the ribcage region (including for example in the lung) is to be validated. Naturally, it is possible to turn at least in part to "natural materials" for the radiation phantom device, such as real bone material, in particular of a human skeleton. Typical radiological absorption properties are 1.25-2 for bone, 0.8-1 (in particular 0.9) for fat, 0-0.7 for the lung and 0 for air (in each case relative to the radiological absorption property of water). An imitation of a model which is as detailed as possible may thus also provide implants and the like. For example, in the ribcage region, implants (for example made of titanium alloys) could be present in the region of the spinal column so as to reinforce it. Naturally, other implant means are also conceivable. The imitation of a real model need not necessarily relate to radiation properties of the model, but may in particular also relate to other effects. For example, it may also relate to "engagement points" of a movement substitute measurement means. In this context, for example expansion measurement strips which are laid around a patient's ribcage should be considered. An optical tracking system comprising a camera system (for example comprising one or a plurality of video cameras), an implanted tracer material in the "tumour region", laser triangulation sensors and other movement substitute measurement means known in the prior art should also be considered. In particular, what are known as "ground truth" methods should be considered. In these methods, a measurement value, for which it is known that it provides comparatively precise values (in the present context for example the position measurement values of the robot arm or else implanted gold sensors which provide movement detection), is used for calibrating the other movement substitute measurement signals. By way of calibration of this type, particularly precise measurement values can typically be obtained by means of the movement substitutes, even under unfavourable constraints.

It is further advantageous for at least one electronic control means, which preferably comprises at least one data storage means and/or at least one data receiving means, to be provided in the radiation phantom device. By means of the at least one data storage means and/or the at least one data receiving means (which may in particular be in the form of a measurement sensor or similar measurement means), it is possible to supply the findings obtained in the radiation phantom device in particular to a quantitative evaluation. For example, the movements of individual radiation phantom device regions can be stored in a temporally and spatially resolved manner. Moreover, in this context not only digital data storage means and/or data recording means should be considered, but also analogue means (such as X-ray-sensitive films and the like). Preferably, the data reception and/or data storage can also be temporally resolved, generally making much higher-quality verification of the radiation process possible. Naturally, it is also possible for the measurement values of the radiation device (or other devices) to be protocolled in. For example, the movements of the individual radiation phantom device regions may be measured in a manner temporally synchronised with the radiation process, stored and subsequently evaluated. Receiving a relatively large number of measurement signals (which may also have a corresponding bandwidth) naturally requires a suitably formed data storage means or data receiving means. In particular, correspondingly many "data tracks" have to be provided (for example by way of correspondingly many measurement channels), which also each have to be able to process a corresponding amount of data. For example, one of the measurement channels could be a video camera, the image data of which are stored in MP4 format. Alternatively, in various data tracks, the time and the respective 6 components of a 6D movement (translation and rotation) are stored for each movement for each region. The data channels must be made correspondingly wide-band. However, the at least one data receiving means may also in addition or alternatively be used for controlling the radiation phantom device. For example, it is possible for particular movement sequences (including irregular movement sequences such as coughing and the like) to be stored in a data storage means and to be able to be "called" during the validation of the radiation. Data receiving means may also be found to be expedient in this connection, for example in that a real patient (possibly subsequently to be treated) or simply an experimenter is "calibrated", and his movements are imitated by the radiation phantom device. This may further also comprise movement substitutes.

Further, the radiation phantom device may comprise at least one detector means. The detector means may in particular be at least one film detector means and/or at least one temporally resolved detector means. Particularly preferably, the detector means (in particular also the film detector means) can be arranged so as to be replaceable. As mentioned previously, particularly precise, in particular also quantitative validations of radiation can be carried out if detector means are used. Although semiconductor detectors and other electronic detectors have gained some significance for receiving data, film detectors still remain a standard means for radiation measurement. Some definitions and regulations are even based on the use of film detector means. In addition or alternatively, temporally resolved detector means, such as semiconductor detectors, preferably what are known as "pinpoint" ionisation chamber detectors, are provided. These do generally have a much worse spatial resolution than film detectors, but the possibility of temporally resolved measurement generally offers advantages which are not to be underestimated. It is particularly advantageous for the two measurement principles (that is to say temporally resolved detector means and film detector means) to be combined with one another in one detector head. In this case, the advantages of both can be exploited. The fact that the detector means can be replaced particularly rapidly makes a rapid change possible, in the event of damage or between two radiation validations (or possibly partial radiation process validations). Quick locks and the like which are known per se can be used for this purpose. In particular when (generally electrically operating) temporally resolved detector means are used, four-pole electrical plug connectors can correspondingly also be used.

A further preferred construction of the radiation phantom device is provided if it is formed modularly at least in part, modules and/or parts of modules in particular being formed so as to be replaceable. In this way, the corresponding parts can be changed in a rapid and simple manner, in such a way that the radiation phantom device can be adapted to different "models" in a rapid, simple and cost-effective manner. This can greatly further increase the particularly universal application of the radiation phantom device.

Furthermore, a method for validating the radiation process is proposed, the radiation process taking place on a radiation phantom device which comprises at least one movement device for moving at least one first sub-region of the radiation phantom device, in particular relative to at least one second sub-region of the radiation phantom device, and the radiation phantom device having radiation properties which are in conformity with the radiation phantom model at least at times and/or at least in regions. When the proposed method is carried out, the aforementioned advantages and properties already occur at least in an analogous manner. It is further possible to develop the method at least analogously within the context of the present description. In particular, it is possible to obtain a correspondingly large amount of measurement data, in such a way that in particular 4D radiation plans can also be validated and optimised. In particular on the basis of (measured) movement data and movement surrogate data, 4D dose distributions can be recalculated and compared with the radiation inputs measured in the radiation phantom device.

In particular, it is possible for a radiation phantom device having the above-disclosed construction to be used at least at times and/or at least in regions for carrying out the method. In this case, the above-disclosed advantages and properties arise in an analogous manner.

In particular, it is possible for the method to be carried out in such a way that interference signals are used, which in particular are stored in a storage means and/or are measured by at least one measurement device. In a development of this type of the method, it is in particular possible to verify "irregular" movements and the effect thereof on the radiation. This may for example involve coughing by a patient (or in the present context by the radiation phantom device), if "a tumour in the chest region" is to be treated. With a method of this type, the radiation phantom device can imitate reality particularly exactly.

Further, it is possible in addition or alternatively to validate the robustness of what are known as "gating" radiation methods. This applies in particular if the aforementioned "superposed" movement patterns are used. Thus for example in "gating" radiation methods the "gating" is often based on the breathing movement. If there is an (additional) tumour movement superposed on the breathing movement, (undesired) side-effects may occur when the tumour is irradiated. With the proposed radiation phantom device or the proposed method, analyses and validations can also be carried out for this purpose.

FIG. 1 is a schematic overview of a radiation phantom measurement construction 1. The radiation phantom measurement construction 1 comprises a plurality of components, which are each explained in the following individually and in relation to one another.

Figure 2:
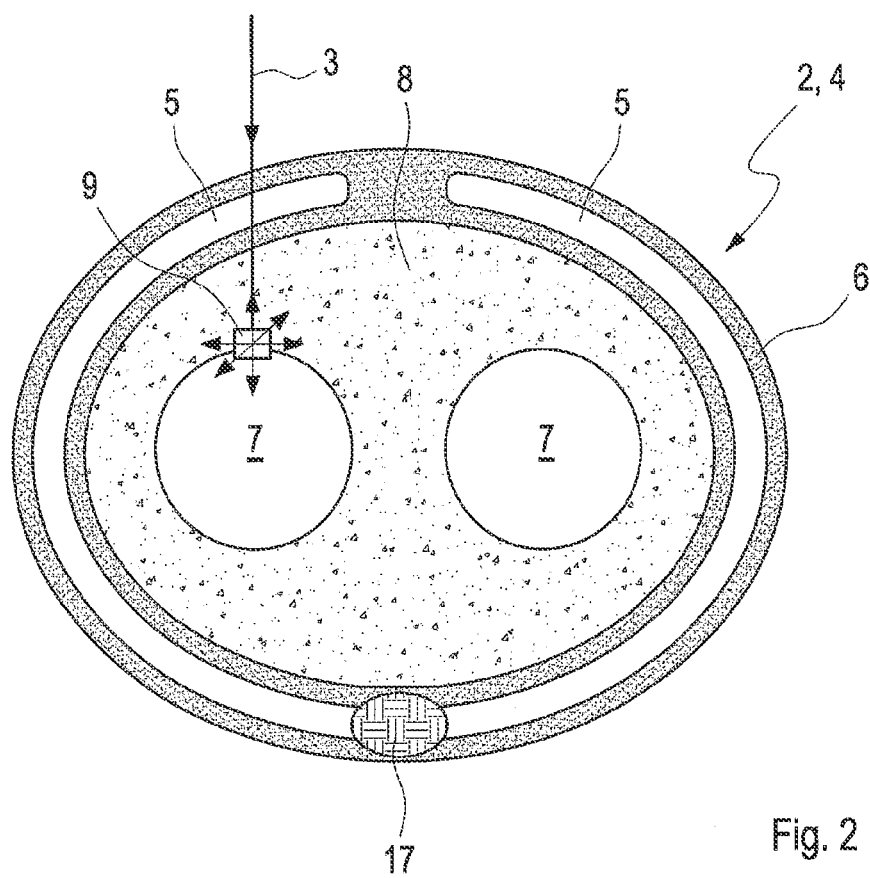
FIG. 2 is a cross-section through one possible embodiment of a radiation phantom.

A major component of the radiation phantom measurement construction 1 is the actual radiation phantom 2 (see also FIG. 2 for this purpose). In the present case, the radiation phantom 2 imitates a ribcage 4, and a tumour which is positioned in the lung tissue is to be treated using a heavy ion beam 3. The heavy ion beam 3 is generated in a manner known per se (typically by means of a linear accelerator and/or a particle synchrotron) and in the present case, in what is known as scanning, guided through the target volume region, which substantially corresponds in the spatial dimensions thereof to the extent of the tumour (plus a safety margin). The calculation method for producing what is known as a radiation plan, that is to say "converting" the predetermined medical conditions into a set of parameters for controlling the particle beam accelerator which generates and suitably deflects the heavy ion beam 3, is known per se and will not be described in greater detail in the following.

For safety reasons, in the present context the calculated radiation plan is to be "shot" into a radiation phantom 2 in advance, so as to test the quality or "correctness" in advance. This may on the one hand be expedient in the real treatment operation, in particular if there is a tumour of a particularly complex form, the tumour is positioned adjacent to a particularly critical tissue region and/or the application method is heavily influenced by the movements of the patient (in such a way that a dosimetric change can be detected). However, validating a radiation plan on a radiation phantom 2 is also advantageous in particular for research purposes, for example so as to develop and check novel calculation algorithms for calculating a radiation plan and/or novel beam control systems, novel beam guidance systems and so forth.

In the present embodiment, the radiation phantom 2 is an "artificial ribcage" 4. Similarly to a "real ribcage", the present ribcage 4 comprises an anatomically correct number of individual ribs 5. In the present case, the ribs are manufactured from a plastics material (PVC in the present case). However, it is equally conceivable for a real human skeleton (of someone who has died) to be used as the basis for the ribcage. The individual ribs 5 are embedded in a thin rubber layer 6. The rubber layer 6 is formed substantially closed (apart from the "upper" and "lower" ends of the ribcage 4) and simulates the radiation properties (optionally including the reflection properties, which are of importance for example when a stereocamera system is used as a movement surrogate) of skin and of muscle tissue. The ribcage 4 is mounted on a base plate made of epoxy resin.

To simulate the lungs, two air-filled balloons 7 are provided, which may optionally be filled with air periodically, at various strengths, via a bellows arrangement, and can thus be enlarged and reduced. The air-filled balloons 7 can be seen particularly clearly in FIG. 2, which is a schematic cross-section through the ribcage 4 of the radiation phantom 2. The air-filled balloons 7 may preferably be filled with a low-density air-permeable foamed material, so as to come as close as possible to the model of real lung tissue (in particular in terms of the radiation properties). The remaining internal tissue of the ribcage 4 is simulated in the present case with a resilient polyurethane foam 8, with which the interior of the ribcage 4 is largely filled (apart from the air-filled balloons 7).

Preferably, the ribcage 4 can be opened using suitable provided interfaces, in such a way that the "soft parts" located therein can be changed in a rapid and simple manner. This relates in particular to the polyurethane foam 8 and to the detector head 9 (including associated "aids" such as the plastics material rod 11). Optionally, it is also possible for the "soft parts" to be pulled out or inserted via the "upper" or "lower" ends of the ribcage 4.

Naturally, other suitable materials may be used instead of the aforementioned materials. In particular, they should come particularly close to the "model" in terms of the properties thereof with respect to radiation (in particular heavy ion radiation 3 of X-ray radiation from a CT).

Since in the presently described embodiment the radiation plan is to be verified for a tumour positioned on a lung, a detector head 9 is in effect provided as a "replacement" for the tumour (or for the target volume region and the volume adjacent thereto), and can be moved in translation in all three spatial directions (each indicated by double-headed arrows in FIGS. 1 and 2). Furthermore, the detector head 9 can also be moved in rotation, but this is not shown in greater detail in the present context for reasons of clarity. One possible construction of a detector head 9 is shown in greater detail in FIG. 3. Preferably, the detector 9 is embedded substantially completely and without gaps in the resilient polyurethane foam 8 surrounding it. When the detector head 9 moves, (at least) the adjacent region of the polyurethane foam 8 thus moves along (including deformations, compressions and expansions induced by this).

In the presently shown embodiment, the detector head 9 can be moved by a commercially available industrial robot 10. Since the industrial robot 10 largely consists of metal, it has to be a certain distance away from the target volume region or the detector head 9, in such a way that the measurement result is not unrealistically distorted. In the presently described embodiment, a plastics material rod 11 is provided for this purpose, and connects the tool socket 12 of the industrial robot 10 to the detector head 9. In addition, thin measurement lines (not shown) for transmitting measurement signals which are obtained in the detector head 9 may be accommodated in the plastics material rod 11. The plastics material rod 11 is manufactured from a suitable plastics material, in such a way that it comes as close as possible to a real ribcage in terms of the properties thereof with respect to radiation (in particular particle radiation and/or X-ray radiation). In this context, it may well be expedient for the plastics material rod 11 to be constructed in a plurality of parts, it being possible to make use of various plastics materials. As can be seen from FIG. 1, the plastics material rod 11 largely extends through the air-filled cavity which is formed by the air-filled balloons 7 (which are optionally filled with an air-permeable foamed material). Optionally, the foamed material may comprise a suitably dimensioned recess for the plastics material rod 11. This results in the smallest possible internal deformation of the polyurethane foam 8 positioned adjacent to the plastics material rod 11 when the plastics material rod 11 moves, which can lead to effects which do not occur in the "original" patient (since a human does not have a structure of this type).

Although this is not shown in greater detail in the present case, it is expedient to provide further detector heads (or optionally also a single additional detector head) in the radiation phantom 2. In particular, detector heads may be provided in the region of (one or more) organs at risk and/or in the region of normal tissue, so as to measure the correspondingly applied radiation dose there. Depending on the requirements, the corresponding detector heads may be configured so as to be moved and/or unmoved.

The industrial robot 10 is controlled by way of a commercially available controller 13. As is conventional, the radiation phantom measurement construction 1 can be monitored by way of one or more user terminals 14.

Further, a stepper motor 15 can be seen in FIG. 1 and is connected to a flexible belt 16 which is laid around the ribcage 4. The arrangement is selected in such a way that the length of the flexible belt 16 can be altered by the stepper motor 15, in such a way that in this way (by cooperation with the resilient construction foam 8) the ribcage 4 can be raised and lowered in a controlled manner. The stepper motor 15 is also controlled by the controller 13 in a suitable manner. Naturally, a plurality of stepper motors 15 and/or of flexible belts 16 may also be provided, and may in particular have a particular mutual lateral offset. A different type of construction would involve the stepper motor 15 controlling a control wire, which (in combination with the resilient properties of the ribcage 4) brings about "physiological" raising and lowering of the ribcage 4.

The stepper motor 15 and the industrial robot 10 may in particular be controlled in such a way that a "mutually superposed" movement of the tumour region, as often observed in real patients, is simulated.

The "raising" and "lowering" of the ribcage 4 does not only have the effect whereby the ribs 5 move in relation to the spinal column 17 and the "tissue" in the inside of the ribcage 4 (that is to say in particular the resilient construction foam 8) can deform (in particular be compressed or expanded). Rather, in reality, the raising and lowering of a ribcage is often used so as to use what is known as a movement substitute signal. Various methods are known for this purpose. One possible method involves taking measurements by means of an expansion measurement strip 18 (known as an ANZAI strip), which is laid around the ribcage 4. In the present context, this method is also used in the radiation phantom measurement construction 1. The data thus obtained are received by a measurement receiver 19 and suitably processed. The output signals of the measurement receiver 19 are used for example so as to readjust the heavy ion beam 3 (for example in what are known as tracking methods) or in extreme cases also to switch it off momentarily. Purely for completeness, it should be noted that in "gating" methods of this type, it is standard for the heavy ion beam 3 to be switched off momentarily.

As can be seen from FIG. 1, by using a (sufficiently rapid) stepper motor 15 and a (sufficiently rapid) industrial robot 10, it is possible both to simulate substantially any desired movement sequences, and furthermore also to simulate very rapid movement sequences. Thus, there is no limitation to a constantly repeating movement pattern, but rather, changes in the patient's breathing pattern can also for example be simulated. In particular, because the stepper motor 15 and the industrial robot 10 can be altered rapidly, rapid movements such as hiccoughs, coughs and the like can also be simulated. Furthermore, it is possible for the stepper motor 15 and the industrial robot 10 to be mutually synchronised, and for it thus to be made possible to analyse temporally varying progressions (for example phase shift between the movements of the "ribcage" and the "tumour"). In particular, effects of this type which may have a relatively large dosimetric effect can be analysed in greater depth. In particular, it is thus possible to check the robustness of a radiation plan or a radiation method against effects of this type.

Figure 3:
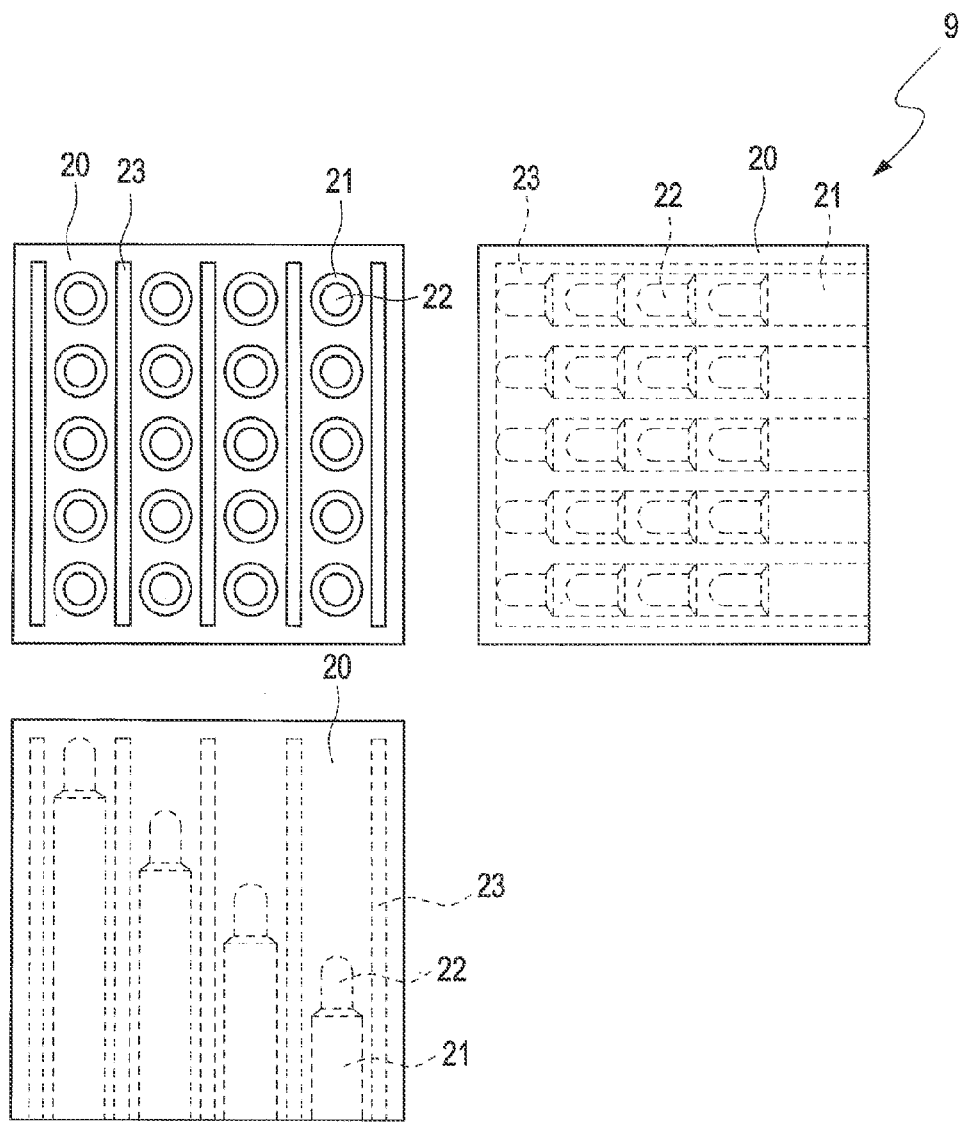
FIG. 3 shows a possible construction of a detector head from different spatial directions, in each case in a schematic plan view.

The detector head 9 is shown in greater depth in FIG. 3 in particular. In this context, the detector head 9 is connected to the plastics material rod 11 (and thus to the industrial robot 10) via a rapid connection. In this way, it is possible to be able to exchange the entire detector head 9 rapidly, for example so as to insert new X-ray films (explained in greater detail below), without the radiation phantom measurement construction 1 being "blocked" for a relatively long period of time. Even if not the entire detector head 9 is changed, the presently selected construction of the detector head 9 comprising slot-like recesses 23 makes it possible to change the X-ray films rapidly, in such a way that idle times can be reduced in this way too.

The detector head 9 is a variation on the detector head disclosed in the publication "A system for three-dimensional dosimetric verification of treatment plans in intensity-modulated radiotherapy with heavy ions", by C. Karger, O Jäkel, G. Hartmann and P. Heeg in Med. Phys. 26(10) dated October 1999, pages 2,125 to 2,132. The substantially cubical base body 20 of the detector head 9 consists of a Plexiglas material. A total of 24 stepped sinkholes 21 of various depths are formed in the base body 20 in an array arrangement (4×5 array). In this context, the position and formation of sinkholes 21 can be seen clearly from the total of three plan views from different spatial directions, which are shown in FIG. 3. The stepped sinkholes 21 serve to accommodate pin-shaped ionisation chambers (known as "pinpoint" ionisation chambers). In this context, the respective front part 22 of the sinkholes 21 accommodates the actual sensitive measurement volume, which typically has a volume of 2-3 mm3 Pin-shaped ionisation chambers of this type have a high measurement precision in terms of the applied dose, and are furthermore also time-resolving. However, the problem therewith is the generally comparatively low spatial resolution.

So as to increase the spatial resolution of the radiation validation, additional slot-like recesses 23 are therefore provided in the presently used detector head 9, and are each formed between two rows of mutually adjacent stepped sinkholes 21. The slot-shaped recesses 23 serve to receive X-ray films. X-ray films have a very high spatial resolution (but a comparatively low dose resolution and no temporal resolution). It may further be expedient for the X-ray films to be located in light-proof protective pouches. In this case, the X-ray films can be handled in daylight, making them much easier to use. In particular, the X-ray films can be changed in the detector head 9 without the need to visit a dark room first.

Using the combination of pin-shaped ionisation chambers and X-ray films, the overall precision of the detector head 9 can be increased greatly. It is therefore particularly suitable for the proposed validation method.

Furthermore, markers or transponders (for example radioopaque) can also be attached in or on the detector head 9, and make it possible to localise (determine the position of) the detector, for example by X-ray or other external monitoring systems. The position is sometimes also determined in this manner in the "real patient", and so the reality can be reproduced particularly precisely in this manner.

Figure 4:
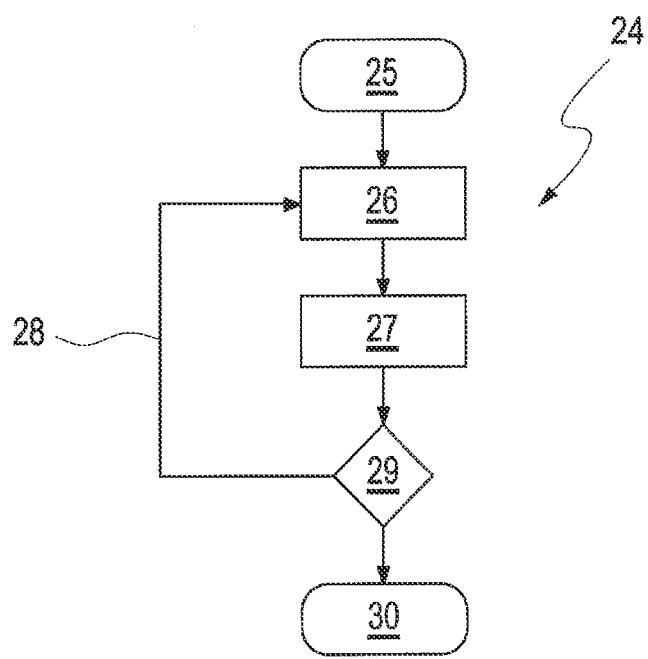
FIG. 4 is a schematic flow chart of a possible method for validating a radiation process.

Finally, FIG. 4 further shows a method 24 for validating a radiation process in a schematic flow chart.

In a first step 25, the provided (calculated) radiation plan, which is subsequently to be applied to the radiation phantom 2, is initially read in. Subsequently, in a second step 26, the actual radiation is carried out. In this context, not only is the heavy ion beam 3 suitably modulated (in particular including as a function of the measurement data supplied from the expansion measurement strip 18 or other measurement devices), but at the same time the radiation phantom 2 is also moved suitably. In this context, suitable movements may in particular also comprise irregular movements such as coughing and the like. In particular, varied correlations between the ribcage 4 and the tumour movement can also be carried out.

During the radiation, the data measured in the detector head 9, which are used for the actual radiation validation, are received in a temporally synchronised manner and stored (step 27). For example, in this context the movements of the detector heads 9, the progression of the movement surrogate (in the present case an expansion measurement strip) 18 and further data of the beam application (in particular the radiation moment of each scanning point) are received and stored. The loop consisting of carrying out radiation 26 and taking measurement values 27 is carried out (return 28) repeatedly until the entire radiation plan has been applied. This is checked in a checking step 29.

If it is established in the checking step 29 that the entire radiation plan has been applied, the method ends 30.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

LIST OF REFERENCE NUMERALS

1 Radiation phantom measurement construction
2 Radiation phantom
3 Heavy ion beam
4 Ribcage
5 Ribs
6 Rubber layer
7 Air-filled balloons
8 Polyurethane foam
9 Detector head
10 Industrial robot
11 Plastics material rod
12 Tool socket
13 Controller
14 User terminal
15 Stepper motor
16 Flexible belt
17 Spinal column
18 Expansion measurement strip
19 Measurement receiver
20 Base body
21 Sinkholes
22 Front part
23 Slot-like recess
24 Method
25 Reading in the radiation plan
26 Carrying out the radiation
27 Receiving data
28 Return
29 Checking step
30 End

The invention claimed is:

1. A radiation phantom device comprising:
at least one movement device for moving at least one first sub-region of the radiation phantom device, the at least one first sub-region resiliently embedded in at least a second sub region of the radiation phantom device wherein the movement device is configured to move the at least one first sub-region relative to the at least one second sub region, and wherein the radiation phantom device has, at least one of at times or in regions, radiation properties which are in conformity with a radiation phantom model.

2. The radiation phantom device recited in claim 1, wherein the radiation phantom device is configured for validating a radiation process.

3. The radiation phantom device recited in claim 2, wherein the radiation phantom device is configured for validating a radiation plan.

4. The radiation phantom device recited in claim 1, further comprising at least one of radiation beam properties or measurement beam properties which are in conformity with the radiation phantom model at least one of at times or in regions.

5. The radiation phantom device recited in claim 1, wherein the radiation phantom device has at least one of weakening properties, secondary radiation emission properties, or scattering properties which are in conformity with the radiation phantom model at least one of at times or in regions.

6. The radiation phantom device recited in claim 5, wherein sub-regions of the radiation phantom device have at least one of weakening properties, secondary radiation emission properties, or scattering properties which are in conformity with the radiation phantom model at least one of at times or in regions, the sub regions being at least one of adjacently, proximally, axially in a disc shape, in a cone shape, or in a fan shape with respect to a target volume region.

7. The radiation phantom device recited in claim 1, wherein the radiation phantom device has at least one of reflection properties or secondary radiation emission properties which are in conformity with the radiation phantom model at least one of at times or in regions.

8. The radiation phantom device recited in claim 1, wherein the at least one movement device is configured to carry out a multi-dimensional movement at least one of at times or in regions.

9. The radiation phantom device recited in claim 1, further comprising a movement transmission device which has radiation properties which are in conformity with the radiation phantom model at least one of at times or in regions.

10. The radiation phantom device recited in claim 1, further comprising at least one movement production device including at least one of an electric motor, a stepper motor, a linear motor, a hydraulic device, a pneumatic device or a robot arm.

11. The radiation phantom device recited in claim 1, wherein the radiation phantom device is configured to imitate a real biological model at least one of at times or in regions.

12. The radiation phantom device recited in claim 1, further comprising an electronic controller.

13. The radiation phantom device recited in claim 1, further comprising at least one detector.

14. The radiation phantom device recited in claim 1, wherein the radiation phantom device is modular.

15. A method for validating a radiation process, comprising:
    irradiating a radiation phantom device including at least one movement device for moving at least one first sub-region thereof, the at least one first sub-region resiliently embedded in at least a second sub region of the radiation phantom device wherein the movement device is configured to move the at least one first sub-region relative to the at least one second sub region, and the radiation phantom device having, at least one of at times or in regions, radiation properties which are in conformity with a radiation phantom model; and
    measuring radiation at the phantom so as to validate the radiation process.

16. The method recited in claim 15, wherein the radiation process is a radiation plan.

17. The method recited in claim 16, wherein the interference signals are at least one of stored in a storage device or measured by a measurement device.

18. The method recited in claim 15, wherein the method is carried out using interference signals.

* * * * *